United States Patent
Pigourier et al.

(10) Patent No.: US 10,669,493 B2
(45) Date of Patent: Jun. 2, 2020

(54) PROCESS AND DEVICE FOR THE INVERTED SEPARATION OF AROMATICS

(71) Applicant: Axens, Rueil-Malmaison (FR)

(72) Inventors: Jérôme Pigourier, Meudon (FR); Isabelle Prevost, Rueil Malmaison (FR)

(73) Assignee: AXENS, Rueil-Malmaison (FR)

( * ) Notice: Subject to any disclaimer, the term of this patent is extended or adjusted under 35 U.S.C. 154(b) by 0 days.

(21) Appl. No.: 16/402,300

(22) Filed: May 3, 2019

(65) Prior Publication Data
US 2019/0338202 A1 Nov. 7, 2019

(30) Foreign Application Priority Data
May 4, 2018 (FR) ..................... 18 53885

(51) Int. Cl.
| | |
|---|---|
| *C10G 61/08* | (2006.01) |
| *B01D 3/14* | (2006.01) |
| *B01D 3/32* | (2006.01) |
| *B01J 19/24* | (2006.01) |
| *C07C 5/27* | (2006.01) |
| *C07C 6/12* | (2006.01) |
| *C07C 7/00* | (2006.01) |
| *C07C 7/04* | (2006.01) |
| *C07C 7/12* | (2006.01) |

(52) U.S. Cl.
CPC ............. *C10G 61/08* (2013.01); *B01D 3/143* (2013.01); *B01D 3/322* (2013.01); *B01J 19/24* (2013.01); *C07C 5/2732* (2013.01); *C07C 6/123* (2013.01); *C07C 7/005* (2013.01); *C07C 7/04* (2013.01); *C07C 7/12* (2013.01); *C10G 2300/1096* (2013.01); *C10G 2300/201* (2013.01); *C10G 2400/30* (2013.01)

(58) Field of Classification Search
CPC ........ B01D 1/28; B01D 1/2856; B01D 3/007; B01D 3/143; B01D 3/146; C07C 15/08; C07C 7/12; C07C 5/2737; C07C 7/005; C07C 7/08; C07C 7/04
See application file for complete search history.

(56) References Cited

U.S. PATENT DOCUMENTS

| | | | |
|---|---|---|---|
| 9,328,040 B2 * | 5/2016 | Corradi | ................... C07C 7/005 |
| 2014/0257010 A1 | 9/2014 | Verba et al. | |
| 2015/0336023 A1 | 11/2015 | Dunet et al. | |

FOREIGN PATENT DOCUMENTS

| | | |
|---|---|---|
| FR | 2 998 301 A1 | 5/2014 |
| FR | 2 998 301 B1 | 1/2016 |

OTHER PUBLICATIONS

Preliminary Search Report for FR 18/53.885, dated Mar. 21, 2019.

\* cited by examiner

*Primary Examiner* — Sharon Pregler
(74) *Attorney, Agent, or Firm* — Fitch, Even, Tabin & Flannery, LLP

(57) ABSTRACT

The present invention relates to a process and to a device for the separation of a feedstock comprising benzene, toluene and C8+ compounds, in which: a toluene column (C10) is fed directly with a C7+ cut resulting from the bottom of a stabilization column (C11) positioned downstream of a transalkylation unit (P4); a C7− cut is withdrawn at the top of the toluene column (C10) and a C8+ cut is withdrawn at the bottom; a benzene column (C9) is fed with the C7− cut resulting from the toluene column (C10); an essentially aromatic cut resulting from an aromatics extraction unit (P1) is injected into the toluene column (C10) separately above the feeding of the C7+ cut or into the benzene column (C9).

21 Claims, 2 Drawing Sheets

PROCESS AND DEVICE FOR THE INVERTED SEPARATION OF AROMATICS

CROSS REFERENCE TO RELATED APPLICATION

Reference is made to French Patent Application No. 18/53.885 filed May 4, 2018, to which priority is claimed and which is incorporated herein by reference in its entirety.

TECHNICAL FIELD

The present invention comes within the field of processes and devices for the separation of aromatic compounds. The object according to the invention applies in particular to the case of an aromatic complex requiring a separation by distillation between benzene, toluene and heavier compounds having 8 or more carbon atoms (hereinafter denoted C8+ compounds).

STATE OF THE ART

Patent FR 2 998 301 B1 describes a method which makes possible an overall energy saving with regard to the fuel and electricity consumption of an aromatic complex for the separation by distillation between benzene, toluene and C8+ compounds. Specifically, the principle of the said method lies in the generation of low-pressure steam in certain columns, the low-pressure steam thus generated being used as heat-exchange fluid, with or without intermediate compression, for example for the reboiling at lower temperature of other columns which have undergone a fall in pressure.

SUMMARY

In the context described above, a first object of the present invention is to make it possible to reduce the amount of energy required to carry out the separation between benzene, toluene and C8+ compounds.

According to a first aspect, the abovementioned object, and also other advantages, are obtained by a process for the separation of a feedstock comprising benzene, toluene and compounds having 8 or more carbon atoms, in a separation device comprising at least one reformate column, one aromatics extraction unit and one transalkylation unit, the effluents from the said units being separated in the following distillation columns: benzene column, toluene column and stabilization column, the said process comprising the following stages:
   the toluene column is fed directly with a C7+ cut resulting from the bottom of the stabilization column positioned downstream of the transalkylation unit in order to withdraw a top product from the toluene column enriched in benzene and in toluene and a bottom product from the toluene column enriched in compounds having 8 or more carbon atoms,
   the benzene column is fed with the top product from the toluene column in order to withdraw a benzene-enriched top product from the benzene column and a toluene-enriched bottom product from the benzene column, and
   the transalkylation unit is fed with the toluene-enriched bottom product from the benzene column,
   in which the toluene column is fed with an essentially aromatic cut resulting from the aromatics extraction unit, the feeding of the toluene column resulting from the aromatics extraction unit being carried out separately from and above the feeding of the toluene column resulting from the bottom of the stabilization column, or
   in which the benzene column is fed with the essentially aromatic cut resulting from the aromatics extraction unit as a mixture with or separately from the top product from the toluene column.

According to one or more embodiments, the toluene column is additionally fed with a top product from the purification column as a mixture with or separately from the C7+ cut resulting from the bottom of the stabilization column.

According to one or more embodiments, the transalkylation unit is additionally fed with a top product from the purification column as a mixture with or separately from the bottom product from the benzene column.

According to one or more embodiments, the separation device additionally comprises a para-xylene separation unit and a xylenes isomerization unit, the said effluents being separated in the following additional distillation columns: xylenes column, heavy aromatics column, raffinate column, extract column, purification column, deheptanizer and stripper.

According to one or more embodiments, only the xylenes column and the heavy aromatics column feeds the transalkylation unit with C9+ aromatic compounds.

According to one or more embodiments, the reformate column is fed with the feedstock in order to produce a C7− cut at the top of the reformate column, and the aromatics extraction unit is fed with the C7− cut in order to extract paraffinic compounds from the C7− cut and to produce the essentially aromatic cut.

According to one or more embodiments, the operating conditions of the benzene column are as follows:
   temperature of 130° C. to 180° C. at the reboiler, from 70° C. to 130° C. at the condenser;
   pressure: between 0.1 MPa and 0.5 MPa; and
   between 35 and 55 theoretical plates.

According to one or more embodiments, the operating conditions of the toluene column are as follows:
   temperature of 130° C. to 260° C. at the reboiler, from 50° C. to 200° C. at the condenser;
   pressure: between 0.05 MPa and 1 MPa; and
   between 30 and 55 theoretical plates.

According to a second aspect, the abovementioned object, and also other advantages, are obtained by a device for the separation of a feedstock comprising benzene, toluene and compounds having 8 or more carbon atoms, the separation device comprising at least one reformate column, one aromatics extraction unit and one transalkylation unit, the separation device additionally comprising the following columns for the distillation of the effluents from the said units: benzene column, toluene column and stabilization column,
   the toluene column being appropriate for being fed with a C7+ cut resulting from the bottom of the stabilization column positioned downstream of the transalkylation unit and for delivering a top product from the toluene column enriched in benzene and in toluene and a bottom product from the toluene column enriched in compounds having 8 or more carbon atoms,
   the benzene column being appropriate for being fed with the top product from the toluene column and for delivering a benzene-enriched top product from the benzene column and a toluene-enriched bottom product from the benzene column, the transalkylation unit being appropriate for treating the toluene-enriched bottom product from the benzene column, in which the toluene column is appropriate for being fed with an essentially aromatic cut resulting from the aromatics extraction unit, the feeding of the toluene column resulting from the aromatics extraction unit being carried out separately from and above the feeding of the toluene column resulting from the bottom of the stabilization column, or in which the benzene column is appropriate for being fed with the essentially aromatic cut resulting from the aromatics extraction unit as a mixture with or separately from the top product from the toluene column.

According to one or more embodiments, the toluene column is suitable for being fed with a top product from a purification column as a mixture with or separately from the C7+ cut resulting from the bottom of the stabilization column.

According to one or more embodiments, the transalkylation unit is suitable for being fed with a top product from a purification column as a mixture with or separately from the bottom product from the benzene column.

According to one or more embodiments, the separation device additionally comprises a para-xylene separation unit, a xylenes isomerization unit and the following additional columns for the distillation of the said effluents: xylenes column, heavy aromatics column, raffinate column, extract column, purification column, deheptanizer and stripper.

According to one or more embodiments, the separation device is appropriate for feeding the reformate column with the feedstock in order to produce a C7− cut at the top of the reformate column, and feeding the aromatics extraction unit with the C7− cut in order to extract paraffinic compounds from the C7− cut and to produce the essentially aromatic cut.

According to one or more embodiments, the operating conditions of the benzene column are as follows:
temperature of 130° C. to 180° C. at the reboiler, from 70° C. to 130° C. at the condenser;
pressure: between 0.1 MPa and 0.5 MPa; and
between 35 and 55 theoretical plates.

According to one or more embodiments, the operating conditions of the toluene column are as follows:
temperature of 130° C. to 260° C. at the reboiler, from 50° C. to 200° C. at the condenser;
pressure: between 0.05 MPa and 1 MPa; and
between 30 and 55 theoretical plates.

Embodiments of the process and of the device which are referenced above and also other characteristics and advantages will become apparent on reading the description which will follow, given solely by way of illustration and without limitation, and with reference to the following drawings.

DETAILED DESCRIPTION

The invention relates to the field of processes and devices for the separation of a feedstock comprising benzene, toluene and C8+ (e.g., C8 to C10) compounds which can in particular comprise para-xylene.

The separation process and device according to the invention can be defined as a series of conversion and separation stages and sections which is intended to separate benzene/toluene/xylenes and/or convert toluene into C8+ compounds and in particular aromatic compounds having eight carbon atoms, known as xylenes, and more particularly para-xylene, starting from a feedstock rich in aromatic compounds ranging from benzene to aromatic compounds having more than 10 carbon atoms (denoted C10+ compounds), for example originating from a catalytic reforming unit. The feedstock rich in aromatic compounds typically exhibits contents of sulfur-containing compounds, nitrogenous compounds and olefin compounds which are very low to zero (e.g. sulfur content <0.5 ppm by weight and/or nitrogen content <0.5 ppm by weight and/or bromine number <1 g/100 g according to ASTM D1159), since these compounds can affect the performance qualities and the lifetime of certain catalysts and molecular sieves employed in the units of the aromatic complex.

The first object according to the invention can be defined as an inversion of the order of the benzene and toluene columns combined with separate feedings of the feedstocks of the columns (which were directed as a mixture to the benzene column according to Patent FR 2 998 301 B1), this being done for a better energy efficiency.

In the description which follows, the term "complex" is used to denote any refining or petrochemical device comprising at least two distillation columns. This definition is very broad and comprises, for example, the device for the catalytic cracking of petrols and the device for the production of para-xylene or meta-xylene from aromatic cuts, known as "aromatic complex". The description which follows and the example which illustrates the separation process and device according to the invention are given in the case of an aromatic complex, but it is clearly understood that an aromatic complex constitutes only one circumstance of application and does not in any way limit the scope of the separation process and device set out in the present description.

Figure 1:
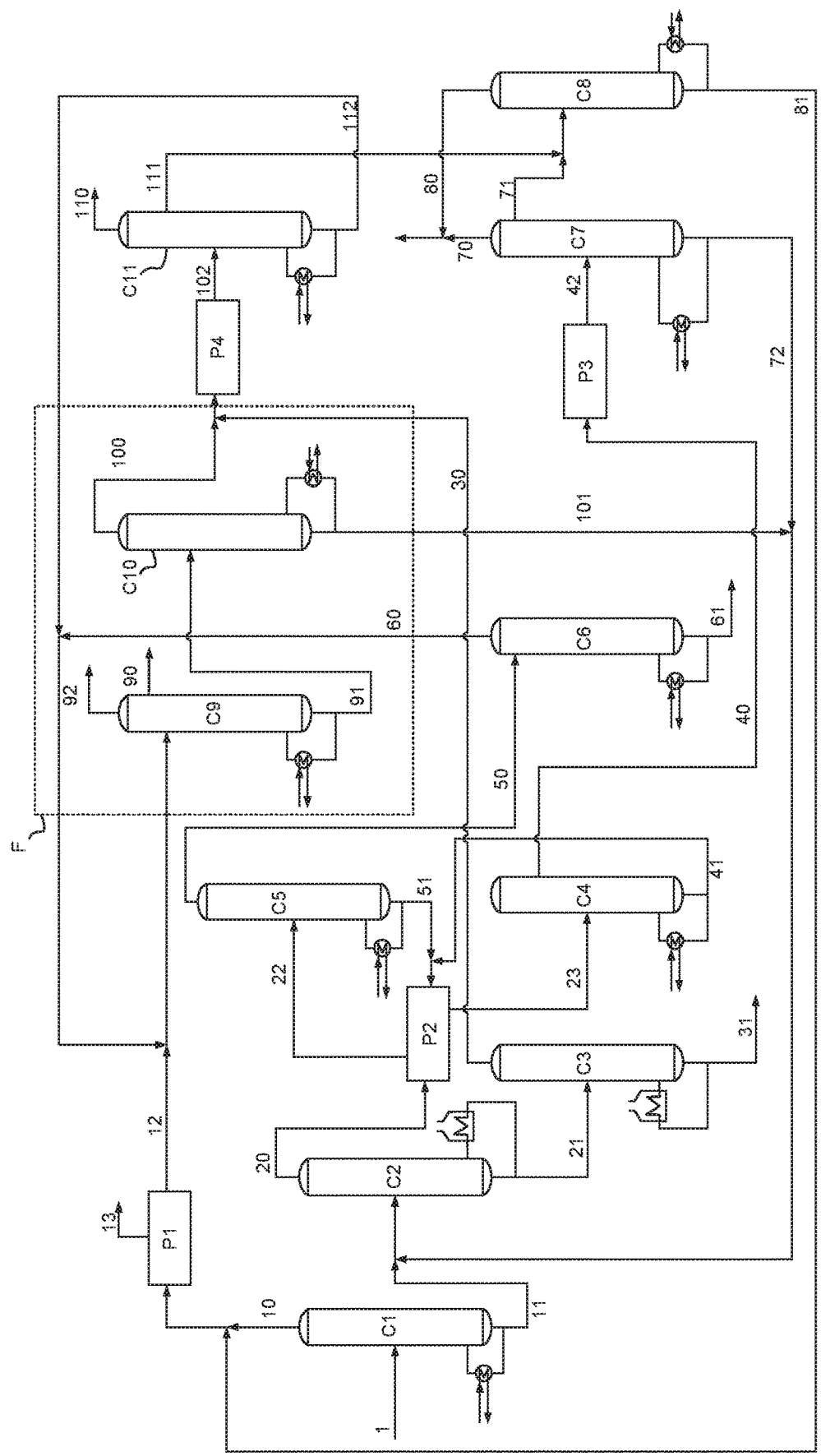
FIG. 1 describes a diagram of an aromatic complex comprising a reference separation section F for the separation of benzene, toluene and C8+ compounds.

FIG. 1 describes a diagram of a reference process and aromatic complex for the separation of benzene, toluene and C8+ compounds.

With reference to FIG. 1, there is in particular described a sequence of two columns, the benzene column C9 and the toluene column C10. This sequence of columns is fed with the mixture of an essentially aromatic C6-C7 cut resulting from the aromatics extraction unit P1 and of a C7+ cut resulting from the bottom of the column of the stabilization column C11 downstream of the transalkylation unit P4. The benzene column C9 produces, at the top, benzene as final product and, at the bottom, a C7+ cut sent to the toluene column C10. The toluene is recovered at the top of the toluene column C10, while a C8+ cut is extracted at the bottom of the toluene column C10.

Figure 2:
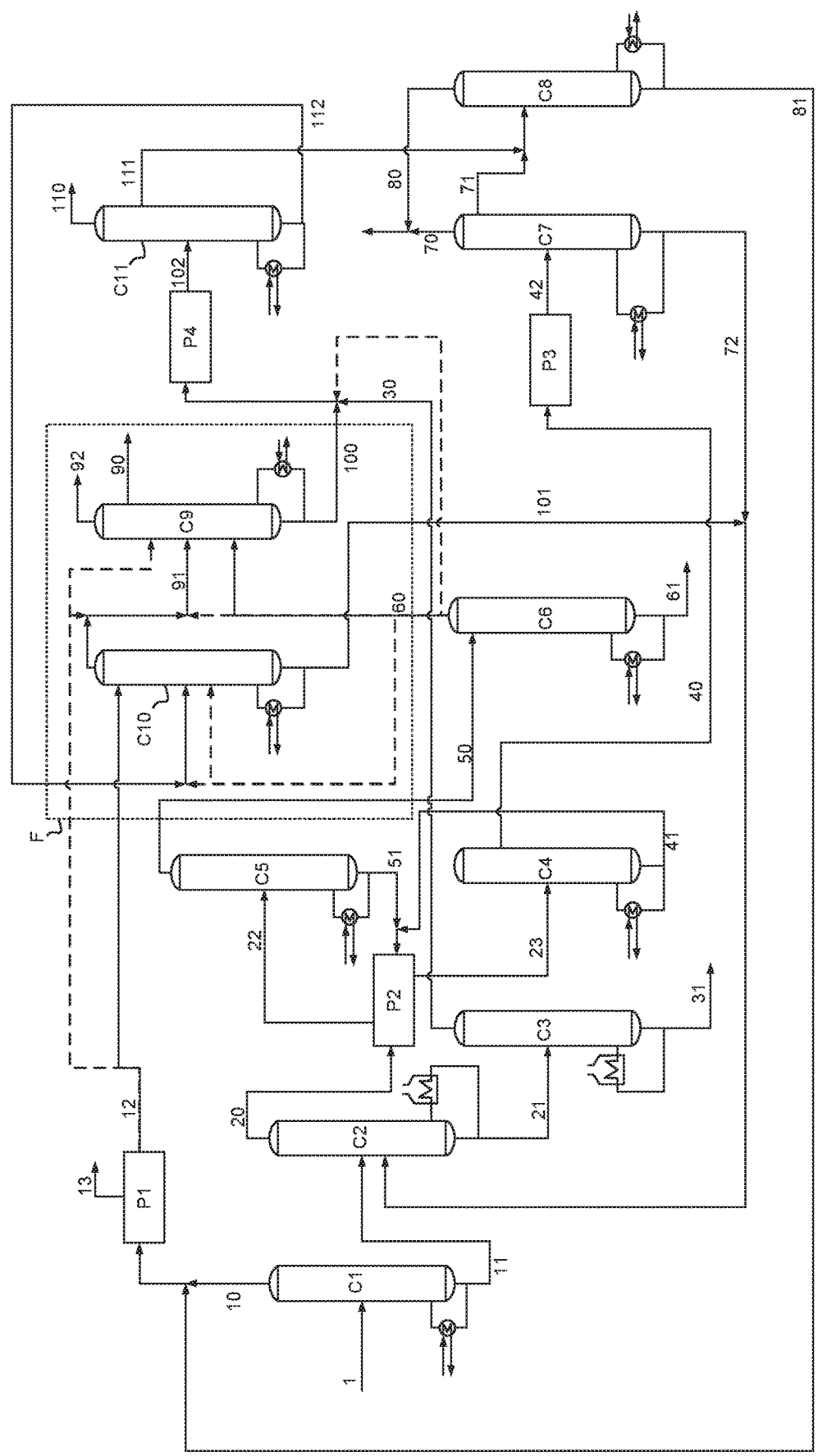
FIG. 2 describes a diagram of an aromatic complex comprising a separation section F according to the invention for the separation of benzene, toluene and C8+ compounds.

FIG. 2 describes a diagram of a separation process and device according to one or more embodiments of the present invention, making it possible in particular to reduce the energy consumption necessary for the separation between benzene, toluene and the C8+ compounds, in comparison with the reference process and aromatic complex.

With reference to FIG. 2, there are in particular described zones of the separation process and device which have been modified so that the toluene column (C10) is fed with a C7+ cut resulting from the bottom of the stabilization column (C11) positioned downstream of the transalkylation unit (P4) in order to withdraw a top product from the toluene column (C10) enriched in benzene and in toluene and a bottom product from the toluene column (C10) enriched in compounds having 8 or more carbon atoms; the benzene column (C9) is fed with the top product from the toluene column (C10) in order to withdraw a benzene-enriched top product from the benzene column (C9) and a toluene-enriched bottom product from the benzene column (C9); and the transalkylation unit (P4) is fed with the toluene-enriched bottom product from the benzene column (C9). According to one or more embodiments, the toluene column (C10) is also fed with an essentially aromatic cut (denoted C6-C7 cut below) resulting from the aromatics extraction unit (P1), the feeding of the toluene column (C10) resulting from the aromatics extraction unit (P1) being carried out separately from and above (downstream of) the feeding of the toluene column (C10) resulting from the bottom of the stabilization column (C11). According to one or more embodiments, the benzene column (C9) is also fed with the C6-C7 cut resulting from the aromatics extraction unit (P1) as a mixture with or separately from the top product from the toluene column (C10).

The conversion and separation stages and sections of the separation process and device according to the invention are described in greater detail below.

When the objective is only to separate the benzene and the C8 compounds and optionally the toluene from a feedstock, only the stages or sections C1, P1, C9, C10, P4 and C11 are presented. The other sections described below are of use only when it is desired to separate the xylenes, indeed even to maximize the para-xylene yield.

Reformate Column C1

The feedstock to be treated is sent, via the line 1, to the first distillation column, denoted reformate column C1, which separates the toluene and the lighter compounds (cut of C7– compounds) from the heavier compounds (cut of C8 to C10+ compounds).

Aromatics Extraction Unit P1

The top effluent from the reformate column C1 is directed to the aromatics extraction unit P1 via the line 10.

The toluene and optionally the compounds recovered at the bottom of the stripper C8 are sent, via the line 81, to the aromatics extraction unit P1.

The aromatics extraction unit P1 separates the essentially aromatic C6-C7 cut from a product comprising paraffinic compounds, which is sent outside the aromatic complex via the line 13. The solvent preferably used in the aromatics extraction unit P1 is N-formylmorpholine (NFM).

With reference to FIG. 1, the C6-C7 cut resulting from the aromatics extraction unit P1 is directed within the separation section F via the line 12 to the benzene column C9.

With reference to FIG. 2, the C6-C7 cut resulting from the aromatics extraction unit P1 is directed within the separation section F via the line 12 either to the benzene column C9 or, in order to be purified from some C8 compounds which it might contain, to the toluene column C10.

According to one or more embodiments, the aromatics extraction unit P1 comprises an extractive distillation unit.

Xylenes Column C2

The C8-C10+ aromatic compounds recovered at the bottom of the column C1 are sent, via the line 11, to the xylenes column C2 in order to separate the C9 and heavier (C9+ compounds) aromatic compounds from a xylenes cut comprising C8 aromatic compounds which feed the units of the aromatic complex which are located downstream.

Para-Xylene Separation Unit P2

The xylenes cut, that is to say the cut of C8 aromatic compounds containing para-xylene, meta-xylene, ortho-xylene and ethylbenzene, is recovered at the top of the xylenes column C2 and is sent, via the line 20, to the para-xylene separation unit P2 which selectively recovers the para-xylene present in the said xylenes cut.

The said para-xylene separation unit P2 can be a para-xylene adsorption unit suitable, for example, for producing a mixture of para-xylene and of desorbent (known as the extract) and a mixture of the other C8– aromatic compounds and of desorbent (known as the raffinate).

The adsorbent used is a molecular sieve dedicated to the adsorption of para-xylene, that is to say that it exhibits a particularly high affinity for this compound.

An adsorbent solid commonly used is a zeolite of faujasite type formed with a siliceous binder, which zeolite is exchanged with barium or with potassium. The desorbent preferably used is para-diethylbenzene (PDEB).

According to one or more embodiments, the para-xylene separation unit P2 comprises a para-xylene crystallization unit, for example as described in U.S. Pat. No. 3,467,724.

According to one or more embodiments, the para-xylene separation unit P2 comprises a combination of a para-xylene adsorption unit and of a crystallization unit as described, for example, in Patent EP-B-053 191.

Extract Column C5

This column is used when the separation unit is of the para-xylene adsorption type. The stream of extract resulting from the para-xylene adsorption unit and containing the para-xylene and desorbent is sent, via the line 22, to the extract column C5 which separates the para-xylene from the desorbent. The desorbent recovered at the bottom of the extract column C5 is sent back to the adsorption column via the line 51. The para-xylene recovered at the top of the extract column C5 is sent to the purification column C6.

Purification Column C6

The top stream from the extract column C5 is sent, via the line 50, to the purification column C6 which separates the toluene (which was partially extracted with the para-xylene) from the para-xylene.

The high-purity para-xylene produced is recovered at the bottom of the purification column C6 and conveyed as finished product by pumping for storage via the line 61.

According to one or more embodiments, the top product from the purification column C6 is directed to the benzene column C9 (line 60) within the separation section F.

With reference to FIG. 2, the top product from the purification column C6 can be: directed either to the benzene column C9, as a mixture with the top stream from the column C10 or via a separate feeding, or to the toluene column C10, for example as a mixture with the C7+ cut resulting from the bottom of the stabilization column C11 (line 112), in order to purify the said top product from some C8 compounds which it might contain; and/or recycled directly to the transalkylation unit P4, for example as a mixture with the C7+ cut extracted at the bottom of the benzene column C9.

Raffinate Column C4

The raffinate originating from the para-xylene separation unit P2 is sent, via the line 23, to the raffinate column C4 which separates the C8 aromatic compounds (raffinate) from the desorbent. The desorbent recovered at the bottom of the column C4 is sent back to the para-xylene adsorption section P2 via the line 41.

The raffinate (C8 aromatics cut) is extracted by sidestream draw-off and sent, via the line 40, as feedstock of the xylenes isomerization unit P3.

Desorbent Column (not Represented)

This column is used when the para-xylene separation unit is of the para-xylene adsorption type. A small portion of the desorbent circulating in the para-xylene adsorption unit is sent to the desorbent column (not represented) so as to remove therefrom the heavy compounds which otherwise would accumulate in the loop.

Xylenes Isomerization Unit P3

The xylenes isomerization unit P3 is used to convert a feedstock depleted in para-xylene into a xylenes stream at thermodynamic equilibrium (denoted "isomerate").

Any type of catalyst capable of isomerizing hydrocarbons having 8 carbon atoms can be used in the separation process and device according to the present invention. A catalyst containing a dehydrogenating metal, such as platinum, palladium or nickel, and an acid phase, for example a doped alumina, a zeolite, such as mordenite, MFI, zeolite Y, or zeolite or non-zeolite molecular sieves comprising an acidity, such as aluminophosphates (e.g. aluminophosphates AlPO, silicoaluminophosphates SAPO), is preferably used. It is thus possible, more preferably, to use an isomerization catalyst comprising a zeolite of EUO structural type, such as zeolite EU1, zeolite ZSM 50 or zeolite TPZ3, as described in patents U.S. Pat. No. 4,640,829, EP-B-042 226 or EP-B-051 318.

Deheptanizer C7

The effluent from the xylenes isomerization unit P3 is sent, via the line 42, to the deheptanizer C7 which separates the isomer (C8+ aromatic compounds) from a C7− light cut recovered at the top of the said deheptanizer column C7. This C7− cut is sent, via the line 71, to the stripper C8 in order to separate the light compounds from the C7− cut.

The C8+ cut, formed of xylenes and heavier compounds, recovered at the bottom of the deheptanizer C7 is recycled, via the line 72, to the xylenes column C2.

In view of the significant content of light (C4−) compounds in the deheptanizer (C7), the top product from the deheptanizer C7 may comprise a vapour phase 70 (predominantly composed of light (C4−) compounds) and a liquid phase 71, both resulting from the reflux drum (not represented).

Stripper C8

The stripper (or stripping column) C8 is fed via the top of the deheptanizer C7.

The stabilized C7− cut is recovered at the bottom of the stripper C8 to be sent to the aromatics extraction unit P1 via the line 81.

The light (C4−) compounds resulting from the stripper top are mixed, via the line 80, with the light compounds from the top of the deheptanizer (line 70) and bled off.

Heavy Aromatics Column C3

The C9+ aromatic compounds recovered at the bottom of the xylenes column C2 are sent, via the line 21, to the heavy aromatics column C3 which separates the C9 and C10 aromatic compounds from the heavier compounds (such as naphthalene) which may have an unfavourable effect on the transalkylation catalyst and which are recovered at the bottom via the line 31.

Transalkylation Unit P4

The C9 and C10 aromatic compounds recovered at the top of the heavy aromatics column C3 are sent, via the line 30, to the transalkylation unit P4.

With reference to FIG. 1, the C9 and C10 aromatic compounds are mixed with the toluene originating from the top of the toluene column C10.

With reference to FIG. 2, the C9 and C10 aromatic compounds are mixed with the toluene originating from the bottom of the benzene column C9.

The transalkylation unit P4 converts the toluene and the C9+ aromatic compounds originating from the reformate column C1 and from the isomerate of the xylenes isomerization unit P3 (after passing through the xylenes column C2 and the heavy aromatics column C3) into a mixture of xylenes and benzene via a thermodynamics-limited reaction. According to one or more embodiments, the xylenes column C2 and the heavy aromatics column C3 provide the majority (substantially all) of the C9+ aromatic compounds sent to the transalkylation unit P4.

Any type of transalkylation catalyst can be used in the separation process and device according to the present invention, for example catalysts based on mordenite or faujasite described in U.S. Pat. No. 3,437,710 or the catalysts based on MCM-22 or beta zeolites described in U.S. Pat. No. 5,030,787 or the catalysts based on mordenite and MFI zeolites as described in Patent Application US 2012/0065446. These catalysts generally additionally comprise a metal compound preferably chosen from the group formed by rhenium, nickel, cobalt, molybdenum, tungsten, palladium and platinum.

Stabilization Column C11

The effluent from the transalkylation unit P4 which contains benzene, unconverted toluene and C8 (e.g. xylenes) and C9+ aromatics is sent, via the line 102, to the stabilization column C11 which separates the compounds lighter than benzene from benzene and heavier aromatic compounds, denoted C7+ compounds.

The gas leaving (the reflux drum of) the stabilization column C11 is sent, via the line 110, to the limit of the aromatic complex.

An unpurified benzene cut is drawn off as a sidestream and sent, via the line 111, to the stripping column C8 which makes it possible to separate the light compounds from the said cut.

According to one or more embodiments, the partial condensation of the top gases from the stabilization column C11 is obtained by means of a cooling tower optionally followed by a water cooler.

Separation Section F

The separation section F comprises the benzene column C9 and the toluene column C10.

Benzene Column C9 According to the Reference Process and Aromatic Complex

With reference to FIG. 1, the C6-C7 cut resulting from the aromatics extraction unit P1 (line 12) is mixed with the C7+ cut resulting from the bottom of the stabilization column C11 (line 112) and sent to the benzene column C9. From the benzene column C9, the benzene is extracted at the top as final product via the line 90. The C7+ cut extracted at the bottom of the benzene column C9 is directed via the line 91 to the toluene column C10.

Toluene Column C10 According to the Reference Process and Aromatic Complex

With reference to FIG. 1, the toluene column C10 is fed with the C7+ cut resulting from the bottom of the benzene column C9. The toluene recovered at the top of the toluene column C10 is directed via the line 100 as feedstock of the transalkylation unit P4. The C8+ cut extracted at the bottom of the column C10 is recycled via the line 101 to the xylenes column C2.

Toluene Column C10 According to the Separation Process and Device According to the Present Invention With reference to FIG. 2, the toluene column C10 is fed with the C7+ cut resulting from the bottom of the stabilization column C11 (line 112). The top product from the toluene column C10 is a cut rich in C7− compounds (e.g., essentially toluene+C6− compounds) and the bottom product is a C8+ cut rich in aromatic compounds having 8 carbon atoms.

The C8+ cut extracted at the bottom of the toluene column C10 (i.e., bottom product from the toluene column C10 enriched in compounds having 8 or more carbon atoms) is recycled, via the line 101, to the xylenes column C2 which separates the C9+ and heavier compounds from the C8 aromatics cut feeding the para-xylene separation device.

According to one or more embodiments, the C6-C7 cut resulting from the aromatics extraction unit P1 is sent to the toluene column C10 in a separate way and above the feeding of the C7+ cut resulting from the bottom of the stabilization column C11.

Since the effluent resulting from the top of the purification column C6 may have a very low flow rate compared with the other two streams treated by the separation section F, according to one or more embodiments of the present invention, the said effluent is mixed with the C7+ cut resulting from the bottom of the column C11. Any other position for feeding the stream resulting from the top of the purification column C6 into the separation section F is possible. For example, the top of the purification column C6 can be recycled to the benzene column C9 or directly to the transalkylation unit P4. It is possible, for example, to feed the transalkylation unit P4 with a mixture comprising the bottom product from the benzene column C9 and a top product from the purification column C6.

According to one or more embodiments, the operating conditions of the toluene column are as follows:
temperature of 130° C. to 260° C. at the reboiler, from 50° C. to 200° C. at the condenser;
pressure: between 0.05 MPa and 1 MPa; and
between 30 and 55 theoretical plates.

Benzene Column C9 According to the Separation Process and Device According to the Present Invention With reference to FIG. 2, the C7− cut extracted at the top of the toluene column C10 (i.e., top product from the toluene column enriched in benzene and in toluene) is directed, via the line 91, to the benzene column C9.

According to one or more embodiments of the present invention, for example when the C6− C7 cut resulting from the aromatics extraction unit P1 contains very little C8+ (for example <1% by weight of C8+ in the C6-C7 cut, preferably <0.5% by weight and more preferably still <0.3% by weight), the C6-C7 cut resulting from the aromatics extraction unit P1 is directed to the benzene column C9 downstream of the toluene column C10 (as a mixture with or separately from the top of the toluene column C10). According to one or more embodiments, the feeding of the benzene column C9 resulting from the aromatics extraction unit P1 is carried out separately from and preferably above (downstream of) the feeding resulting from the top of the toluene column C10.

Starting from the benzene column C9, the benzene-enriched top product is extracted as final product via the line 90. According to one or more embodiments, the benzene-enriched product is extracted by sidestream draw-off. According to one or more embodiments, light and non-condensable compounds are bled off via a vapour stream at the column top (line 92). The toluene-enriched bottom product from the benzene column C9 is directed, via the line 100, to the transalkylation unit P4.

According to one or more embodiments, the operating conditions of the benzene column are as follows:
temperature of 130° C. to 180° C. at the reboiler, from 70° C. to 130° C. at the condenser;
pressure: between 0.1 MPa and 0.5 MPa; and
between 35 and 55 theoretical plates.

In FIGS. 1 and 2, for reasons of simplicity, the reflux sections, reflux drums or condensers are not represented; any known condensation means (for example: cooling tower and/or water cooler) can be used.

EXAMPLES

In the examples, the separation section F is fed with the two following feedstocks:
Feedstock 1: the C6-C7 cut resulting from the aromatics extraction unit P1; and
Feedstock 2: the C7+ cut resulting from the bottom of the stabilization column C11.

In the examples, the top of the purification column C6 is recycled directly to the transalkylation unit P4.

Example 1

The compositions of the two feedstocks (Feedstock 1 and Feedstock 2) of the separation section F are shown in Table 1.

TABLE 1

|  |  | Feedstock 1 | Feedstock 2 |
|---|---|---|---|
| Benzene | kg/hr | 21 406 | 12 297 |
| Other C6 compounds | kg/hr | 0 | 27.2 |
| Toluene | kg/hr | 45 521 | 62 585 |
| Other C7 compounds | kg/hr | 0.1 | 15 |
| Ethylbenzene | kg/hr | 130 | 339 |
| Xylenes | kg/hr | 636 | 51 744 |
| Other C8 compounds | kg/hr | 0.9 | 0.9 |
| C9+ compounds | kg/hr | 0 | 18 682 |

The cuts exiting from the separation section F are products respectively enriched in benzene, toluene and C8+ compounds, according to the compositions of Table 2.

TABLE 2

|  |  | Product enriched in benzene | Product enriched in toluene | Product enriched in C8+ compounds |
|---|---|---|---|---|
| Benzene | kg/hr | 33 534 | 168 | 0 |
| Other C6 compounds | kg/hr | 27 | 0 | 0 |
| Toluene | kg/hr | 1 | 107 842 | 263 |
| Other C7 compounds | kg/hr | 0 | 15 | 0 |
| Ethylbenzene | kg/hr | 0 | 9 | 460 |
| Xylenes | kg/hr | 0 | 256 | 52 124 |
| Other C8 compounds | kg/hr | 0 | 2 | 0 |
| C9+ compounds | kg/hr | 0 | 0 | 18 682 |

Four fractionation configurations are evaluated:
Configuration 1 (according to the reference separation process and device): the benzene column is fed with the mixture of the two feedstocks. The bottom of the benzene column feeds the toluene column.

Configuration 2 (comparative): the benzene column is fed with the two feedstocks introduced separately into the column. The bottom of the benzene column feeds the toluene column.

Configuration 3 (comparative): the toluene column is fed with the mixture of the two feedstocks. The top of the toluene column feeds the benzene column.

Configuration 4 (according to the separation process and device according to the invention): the toluene column is fed with the two feedstocks introduced separately into the column. Feedstock 1 is fed above Feedstock 2. The top of the toluene column feeds the benzene column.

The positions of the feedings are optimized in each of the configurations so as to minimize the reboiling energy consumptions of each of the columns.

The geometries and energy consumptions of each of the configurations are shown in Table 3.

It is noticed that, surprisingly, it is only by inverting the order of the columns and by introducing the two feedstocks separately (configuration 4 according to the invention) that a significant (greater than 10%) energy saving is obtained, in comparison with the reference example. The simple inversion of the columns (configuration 3) or the separate introduction of the two feedings (configuration 2), carried out independently of one another, does not make it possible to obtain a significant energy saving.

In this example, the choice is made to direct the C6-C7 cut resulting from the aromatics extraction unit P1 directly to the benzene column C9 when the latter is downstream of the toluene column C10 as its content of C8+ compounds (767 kg/hr) is greater than the content of C8+ compounds which is desired in the bottom product from the toluene column C10 (267 kg/hr).

Example 2

The compositions of the 2 feedstocks in the benzene, toluene, C8+ compounds separation section (F) are shown in Table 4.

TABLE 4

|  |  | Feedstock 1 | Feedstock 2 |
|---|---|---|---|
| Benzene | kg/hr | 21 406 | 12 297 |
| Other C6 compounds | kg/hr | 0 | 27.2 |
| Toluene | kg/hr | 45 521 | 62 585 |
| Other C7 compounds | kg/hr | 0 | 15 |
| Ethylbenzene | kg/hr | 32 | 339 |
| Xylenes | kg/hr | 159 | 51 744 |
| Other C8 compounds | kg/hr | 1 | 0.9 |
| C9+ compounds | kg/hr | 0 | 18 682 |

In this example, the content of C8+ compounds (192 kg/hr) in Feedstock 1 makes it possible, in the diagram according to the invention where the benzene column C9 is downstream of the toluene column C10, to directly direct the Feedstock 1 resulting from the C6/C7 cut resulting from the aromatics separation unit P1 to the benzene column C9.

Three fractionation configurations are evaluated:

Configuration 1 (according to the reference separation process and device): the benzene column is fed with the mixture of the 2 feedstocks. The bottom of the benzene column feeds the toluene column.

Configuration 5 (according to the invention): the toluene column is fed solely with Feedstock 2. Feedstock 1 is mixed at the top of the toluene column. This mixture feeds the benzene column.

Configuration 6 (according to the invention): the toluene column is fed solely with Feedstock 2. Feedstock 1 and the top of the toluene column feed the benzene column separately, The cuts exiting from the separation section F are products respectively enriched in benzene, toluene and C8+ compounds, according to the compositions of Table 5 according to Configuration 1 and of Table 6 according to Configurations 5 and 6.

TABLE 3

|  | Configuration 1 | Configuration 2 | Configuration 3 | Configuration 4 |
|---|---|---|---|---|
| Feeding of the benzene column C9 | Feedstock 1 and 2 mixed | Feedstock 1 and 2 separated | Top of the toluene column | Top of the toluene column |
| Number of plates benzene column C9 | 38 | 38 | 38 | 38 |
| Feeding plate benzene column C9 | 22 | Feedstock 1: 20 Feedstock 2: 24 | 22 | 22 |
| Feeding of the toluene column C10 | Bottom of the benzene column | Bottom of the benzene column | Feedstock 1 and 2 mixed | Feedstock 1 and 2 separated |
| Number of plates toluene column C10 | 30 | 30 | 30 | 30 |
| Feeding plate toluene column C10 | 16 | 16 | 17 | Feedstock 1: 5 Feedstock 2: 18 |
| Energy consumption in the reboiler of the benzene column C9 (MW) | 23.9 | 22.6 | 22.1 | 22.1 |
| Energy consumption in the reboiler of the toluene column C10 (MW) | 29.8 | 29.8 | 33 | 24.2 |
| Total energy consumption of the reboilers (MW) | 53.7 | 52.4 | 55.1 | 46.3 |

TABLE 5

|  |  | Product enriched in benzene | Product enriched in toluene | Product enriched in C8+ compounds |
|---|---|---|---|---|
| Benzene | kg/hr | 33 534 | 168 | 0 |
| Other C6 compounds | kg/hr | 27 | 0 | 0 |
| Toluene | kg/hr | 1 | 107 845 | 260 |
| Other C7 compounds | kg/hr | 0 | 15 | 0 |
| Ethylbenzene | kg/hr | 0 | 7 | 364 |
| Xylenes | kg/hr | 0 | 259 | 51 644 |
| Other C8 compounds | kg/hr | 0 | 2 | 0 |
| C9+ compounds | kg/hr | 0 | 0 | 18 682 |

TABLE 6

|  |  | Product enriched in benzene | Product enriched in toluene | Product enriched in C8+ compounds |
|---|---|---|---|---|
| Benzene | kg/hr | 33 534 | 168 | 0 |
| Other C6 compounds | kg/hr | 27 | 0 | 0 |
| Toluene | kg/hr | 1 | 107 844 | 260 |
| Other C7 compounds | kg/hr | 0 | 15 | 0 |
| Ethylbenzene | kg/hr | 0 | 42 | 338 |
| Xylenes | kg/hr | 0 | 224 | 51 721 |
| Other C8 compounds | kg/hr | 0 | 2 | 0 |
| C9+ compounds | kg/hr | 0 | 0 | 18 682 |

The content of C8+ compounds in Feedstock 1 is sufficiently low for it to be possible to obtain the same content of C8+ compounds in the product enriched in toluene in Configurations 5 and 6 (268 kg/hr) as in Configuration 1.

The positions of the feedings are optimized in each of the configurations so as to minimize the reboiling energy consumptions of each of the columns.

The geometries and energy consumptions of each of the configurations are shown in Table 7.

TABLE 7

|  | Configuration 1 | Configuration 5 | Configuration 6 |
|---|---|---|---|
| Feeding of the benzene column C9 | Feedstock 1 and 2 mixed | Top of the toluene column and Filler 1 mixed | Top of the toluene column and Filler 1 separated |
| Number of plates benzene column C9 | 38 | 38 | 38 |
| Feeding plate benzene column C9 | 22 | 22 | Top of the toluene column: 28 Feedstock 1: 22 |
| Feeding of the toluene column C10 | Bottom of the benzene column | Feedstock 2 | Feedstock 2 |
| Number of plates toluene column C10 | 30 | 30 | 30 |
| Feeding plate toluene column C10 | 16 | 18 | 18 |
| Energy consumption in the reboiler of the benzene column C9 (MW) | 23.9 | 21.7 | 18.8 |
| Energy consumption in the reboiler of the toluene column C10 (MW) | 29.7 | 24.0 | 24.0 |
| Total energy consumption of the reboilers (MW) | 53.6 | 45.7 | 42.81 |

Configurations 5 and 6 according to the invention are more efficient energetically than Configuration 1 according to the reference separation process and device.

The invention claimed is:

1. Process for the separation of a feedstock comprising benzene, toluene and compounds having 8 or more carbon atoms, in a separation device comprising at least one reformate column (C1), one aromatics extraction unit (P1) and one transalkylation unit (P4), the effluents from the units being separated in the following distillation columns: benzene column (C9), toluene column (C10) and stabilization column (C11), the process comprising the following stages:

feeding the toluene column (C10) directly with a C7+ cut recovered from the bottom of the stabilization column (C11) positioned downstream of the transalkylation unit (P4) and withdrawing a top product from the toluene column (C10) enriched in benzene and in toluene and a bottom product from the toluene column (C10) enriched in compounds having 8 or more carbon atoms, feeding the benzene column (C9) with the top product from the toluene column (C10) and withdrawing a benzene-enriched top product from the benzene column (C9) and a toluene-enriched bottom product from the benzene column (C9), and feeding the transalkylation unit (P4) with the toluene-enriched bottom product from the benzene column (C9), and further comprising in addition to feeding the toluene column (C10) directly with a C7+ cut recovered from the bottom of the stabilization column (C11) positioned downstream of the transalkylation unit (P4), separately feeding the toluene column (C10) with an essentially aromatic cut resulting from the aromatics extraction unit (P1) to a position above a position at which the toluene column (C10) is fed with the C7+ cut recovered from the bottom of the stabilization column (C11), or feeding the benzene column (C9) with the essentially aromatic cut resulting from the aromatics extraction unit (P1) as a mixture with or separately from the top product from the toluene column (C10).

2. Separation process according to claim 1, in which the toluene column (C10) is additionally fed with a top product from the purification column (C6) as a mixture with or separately from the C7+ cut resulting from the bottom of the stabilization column (C11).

3. Separation process according to claim 1, in which the transalkylation unit (P4) is additionally fed with a top product from the purification column (C6) as a mixture with or separately from the bottom product from the benzene column (C9).

4. Separation process according to claim 1, in which the separation device additionally comprises a para-xylene separation unit (P2) and a xylenes isomerization unit (P3), the effluents being separated in the following additional distillation columns: xylenes column (C2), heavy aromatics column (C3), raffinate column (C4), extract column (C5), purification column (C6), deheptanizer (C7) and stripper (C8).

5. Separation process according to claim 4, in which only the xylenes column (C2) and the heavy aromatics column (C3) feed the transalkylation unit (P4) with C9+ aromatic compounds.

6. Separation process according to claim 1, in which the reformate column (C1) is fed with the feedstock in order to produce a C7− cut at the top of the reformate column (C1), and the aromatics extraction unit (P1) is fed with the C7− cut in order to extract paraffinic compounds from the C7− cut and to produce the essentially aromatic cut.

7. Separation process according to claim 1, the operating conditions of the benzene column (C9) are as follows:
    temperature of 130° C. to 180° C. at the reboiler, from 70° C. to 130° C. at the condenser;
    pressure: between 0.1 MPa and 0.5 MPa; and
    the benzene column (C9) comprising between 35 and 55 theoretical plates.

8. Separation process according to claim 1, the operating conditions of the toluene column (C10) are as follows:
    temperature of 130° C. to 260° C. at the reboiler, from 50° C. to 200° C. at the condenser;
    pressure: between 0.05 MPa and 1 MPa; and
    the toluene column (C10) comprising between 30 and 55 theoretical plates.

9. Device for the separation of a feedstock comprising benzene, toluene and compounds having 8 or more carbon atoms, the separation device comprising at least one reformate column (C1), one aromatics extraction unit (P1) and one transalkylation unit (P4), the separation device additionally comprising the following columns for the distillation of the effluents from the units: benzene column (C9), toluene column (C10) and stabilization column (C11),
    the toluene column (C10) being configured to receive a C7+ cut recovered from the bottom of the stabilization column (C11) positioned downstream of the transalkylation unit (P4) and to deliver a top product from the toluene column (C10) enriched in benzene and in toluene and a bottom product from the toluene column (C10) enriched in compounds having 8 or more carbon atoms,
    the benzene column (C9) being configured to receive the top product from the toluene column (C10) and to deliver a benzene-enriched top product from the benzene column (C9) and a toluene-enriched bottom product from the benzene column (C9), and
    the transalkylation unit (P4) being configured to treat the toluene-enriched bottom product from the benzene column (C9), wherein:
    in addition to the toluene column (C10) being configured to receive a C7+ cut resulting from the bottom of the stabilization column (C11), the toluene column (C10) is also configured to separately receive an essentially aromatic cut resulting from the aromatics extraction unit (P1) at a position above a position at which the toluene column (C10) receives the C7+ cut recovered from the bottom of the stabilization column (C11), or wherein
    the benzene column (C9) is configured to receive the essentially aromatic cut resulting from the aromatics extraction unit (P1) as a mixture with or separately from the top product from the toluene column (C10).

10. Separation device according to claim 9, in which the toluene column (C10) is appropriate for being fed with a top product from a purification column (C6) as a mixture with or separately from the C7+ cut resulting from the bottom of the stabilization column (C11).

11. Separation device according to claim 9, in which the transalkylation unit (P4) is appropriate for being fed with a top product from a purification column (C6) as a mixture with or separately from the bottom product from the benzene column (C9).

12. Separation device according to claim 9, additionally comprising a para-xylene separation unit (P2), a xylenes isomerization unit (P3) and the following additional columns for the distillation of the effluents: xylenes column (C2), heavy aromatics column (C3), raffinate column (C4), extract column (C5), purification column (C6), deheptanizer (C7) and stripper (C8).

13. Separation device according to claim 9, in which the reformate column (C1) is appropriate for being fed with the feedstock in order to produce a C7− cut at the top of the reformate column (C1), and the aromatics extraction unit (P1) is appropriate for being fed with the C7− cut in order to extract paraffinic compounds from the C7− cut and to produce the essentially aromatic cut.

14. Separation device according to claim 9, in which the benzene column (C9) is appropriate for being used under the following operating conditions:
    temperature of 130° C. to 180° C. at the reboiler, from 70° C. to 130° C. at the condenser;
    pressure: between 0.1 MPa and 0.5 MPa; and
    the benzene column (C9) comprising between 35 and 55 theoretical plates.

15. Separation device according to claim 9, in which the toluene column (C10) is appropriate for being used under the following operating conditions:
    temperature of 130° C. to 260° C. at the reboiler, from 50° C. to 200° C. at the condenser;
    pressure: between 0.05 MPa and 1 MPa; and
    the toluene column (C10) comprising between 30 and 55 theoretical plates.

16. Separation device according to claim 9, wherein, in addition to the toluene column (C10) being configured to receive a C7+ cut resulting from the bottom of the stabilization column (C11), the toluene column (C10) is also configured to separately receive an essentially aromatic cut resulting from the aromatics extraction unit (P1) at a position above a position at which the toluene column (C10) receives the C7+ cut recovered from the bottom of the stabilization column (C11).

17. Separation device according to claim 9, wherein the benzene column (C9) is configured to receive the essentially aromatic cut resulting from the aromatics extraction unit (P1) as a mixture with or separately from the top product from the toluene column (C10).

18. Separation device according to claim 9, wherein, in addition to the toluene column (C10) being configured to receive a C7+ cut resulting from the bottom of the stabilization column (C11), the toluene column (C10) is also configured to separately receive an essentially aromatic cut resulting from the aromatics extraction unit (P1) at a position above a position at which the toluene column (C10) receives the C7+ cut recovered from the bottom of the stabilization column (C11) and wherein the benzene column (C9) is configured to receive the essentially aromatic cut resulting from the aromatics extraction unit (P1) as a mixture with or separately from the top product from the toluene column (C10).

19. Separation process according to claim 1, wherein, in addition to feeding the toluene column (C10) directly with a C7+ cut recovered from the bottom of the stabilization column (C11) positioned downstream of the transalkylation unit (P4), the process further comprises separately feeding the toluene column (C10) with an essentially aromatic cut resulting from the aromatics extraction unit (P1) to a position above a position at which the toluene column (C10) is fed with the C7+ cut recovered from the bottom of the stabilization column (C11).

20. Separation process according to claim 1, wherein the process further comprises feeding the benzene column (C9) with the essentially aromatic cut resulting from the aromatics extraction unit (P1) as a mixture with or separately from the top product from the toluene column (C10).

21. Separation process according to claim 1, wherein the process further comprises, in addition to feeding the toluene column (C10) directly with a C7+ cut recovered from the bottom of the stabilization column (C11) positioned downstream of the transalkylation unit (P4), separately feeding the toluene column (C10) with an essentially aromatic cut resulting from the aromatics extraction unit (P1) to a position above a position at which the toluene column (C10) is fed with the C7+ cut recovered from the bottom of the stabilization column (C11), and further comprises feeding the benzene column (C9) with the essentially aromatic cut resulting from the aromatics extraction unit (P1) as a mixture with or separately from the top product from the toluene column (C10).

\* \* \* \* \*